United States Patent [19]

Lumma, Jr. et al.

[11] 4,082,844
[45] * Apr. 4, 1978

[54] 6-CHLORO-2-(1-PIPERAZINYL)PYRAZINE

[75] Inventors: William C. Lumma, Jr., Pennsburg; Walfred S. Saari, Lansdale, both of Pa.

[73] Assignee: Merck & Co., Inc., Rahway, N.J.

[*] Notice: The portion of the term of this patent subsequent to Mar. 28, 1995, has been disclaimed.

[21] Appl. No.: 696,255

[22] Filed: Jun. 15, 1976

Related U.S. Application Data

[63] Continuation-in-part of Ser. No. 656,664, Feb. 9, 1976, abandoned, which is a continuation-in-part of Ser. No. 570,052, Apr. 21, 1975, abandoned.

[51] Int. Cl.$^2$ .................. A61K 31/495; C07D 241/10
[52] U.S. Cl. ................................ 424/250; 260/268 H
[58] Field of Search .................... 260/268 H; 424/250

[56] References Cited

U.S. PATENT DOCUMENTS 2,606,906  8/1952  Hultquist et al. .................... 260/268

Primary Examiner—Donald G. Daus
Assistant Examiner—Lisa Jones
Attorney, Agent, or Firm—Rudolph J. Anderson, Jr.; Harry E. Westlake, Jr.; William H. Nicholson

[57] ABSTRACT

The compound 6-chloro-2-(1'-piperazinyl)pyrazine, its N-oxides and acid-addition salts are disclosed having pharmacological activity as anorexic agents.

3 Claims, No Drawings

6-CHLORO-2-(1-PIPERAZINYL)PYRAZINE

BACKGROUND OF THE INVENTION

This application is a continuation-in-part of copending application Ser. No. 656,664, filed Feb. 9, 1976, (now abandoned) which in turn is a continuation-in-part of Ser. No. 570,052, filed Apr. 21, 1975 (now abandoned).

This invention relates to new compounds having anorexic activity, to methods of preparing the new compounds, to pharmaceutical formulations containing the new compounds, and to methods of administering the anorexic agents to an animal or human.

Obesity is a fairly common condition and a potentially serious one in view of the correlation between incidence of various diseases and the degree to which a person is overweight. For example, obese persons succumb statistically more frequently to cardiovascular renal disease than do persons of normal weight. Obesity likewise results in higher death rates from diabetes, nephritis, pneumonia, cirrhosis, appendicitis and postoperative complications. Since obesity often occurs simply as a consequence of excessive intake of calories, good management of the condition in these cases can be achieved by restricting the caloric intake. Frequently, however, the patient has difficulty in initiating and maintaining dietary restrictions, making it necessary to employ anorexigenic drugs as adjuvants to therapy.

Accordingly, it is an object of the present invention to provide the novel 6-chloro-2-(1'-piperazinyl)pyrazine, its N-oxides and pharmaceutically acceptable salts which are effective, potent and nontoxic anorexic agents. Another object is to provide pharmaceutical formulations for administration of the anorexic agents. Further objects are to provide methods for preparing the novel compounds and for administering the anorexic agents of the present invention to a mammalian animal or human.

DETAILED DESCRIPTION

The piperazinylpyrazine compound of the present invention has the structural formula:

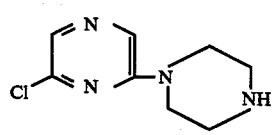

or N-oxide, or a pharmaceutically acceptable salt thereof.

The compound of the present invention is prepared by reaction of a 2-X-pyrazine of formula I with piperazine.

The reaction sequence is as follows:

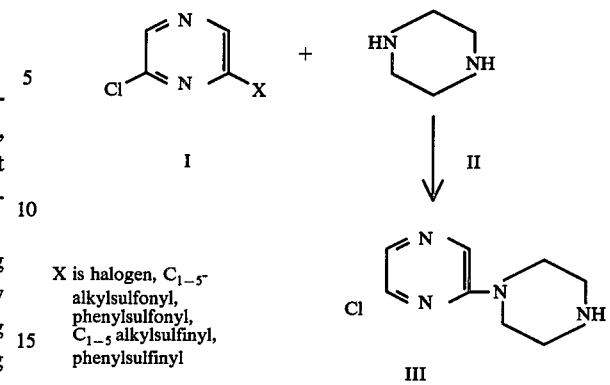

X is halogen, $C_{1-5}$-alkylsulfonyl, phenylsulfonyl, $C_{1-5}$ alkylsulfinyl, phenylsulfinyl The reaction takes place at temperatures ranging from about ambient to about 90° C., preferably under an inert atmosphere, e.g. $N_2$, He or Ar, until a substantial amount of desired adduct of formula III is obtained, typically for a period of from about 0.5 to about 6 hours, preferably from about 1 to about 4 hours.

The compounds of the present invention may be administered as anorexic agents to mammalian species, in amounts ranging of from about 0.01 to about 20 mg. per kg. of body weight, preferably from about 0.1 to about 10 mg. per kg. of body weight in a single dose or in 2 to 4 divided doses.

The compounds of the present invention in the described dosages may be administered orally; however, other routes such as intraperitoneally, subcutaneously, intramuscularly, or intravenously may be employed.

The active compounds of the present invention are administered orally, for example, with an inert diluent or with an assimilable edible carrier, or they may be enclosed in hard or soft gelatin capsules, or they may be compressed into tablets, or they may be mixed with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules, and the like, may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate, and a sweetening agent such as sucrose, lacrose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compound, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

The compounds of the present invention show enhanced effectiveness and less toxicity than known anorexic agents. The 6-chloro-2-(1'-piperazinyl)pyrazine compound, for example, is more effective than fenfluramine in the cat following oral administration.

In addition to the anorexic activity described above, the novel compounds of this invention pharmacologically influence serotonin levels in a manner that suggests they are also useful as antidepressant, antihypertensive, analgesic and sleep inducing agents. For these purposes, the same routes of administration, and pharmaceutical formulations as described above would be employed.

The following examples illustrate the present invention without, however, limiting the same thereto. Unless otherwise indicated, all temperatures are expressed in degrees Celsius.

EXAMPLE 1

6-Chloro-2(1'-piperazinyl)pyrazine hydrochloride 2,6-Dichloropyrazine (0.10 mole) is added to 20 g. piperazine in 200 ml. acetonitrile and the mixture refluxed 1.5 hr. under $N_2$. The mixture is concentrated in vacuo and the residue partitioned between 1N aqueous NaOH and benzene. The combined benzene extracts are washed with 1N aqueous NaOH, dried over $MgSO_4$, filtered and concentrated in vacuo to a yellow oil which is dissolved in 200 ml. absolute ethanol containing 10 ml. of cold, saturated anhydrous ethanolic HCl. The precipitated hydrochloride is recrystallized from 95% ethanol to give faintly yellow needles, m.p. 350° dec.

EXAMPLE 2

6-Chloro-2-(1'-piperazinyl)-pyrazine-1-oxide

2-Chloropyrazine (0.1 mole) is added to a solution of 0.3 mole trifluoroperacetic acid in $CH_2Cl_2$ (300 ml.) at 0°. The mixture is stirred 4 hours at 0°, 4 hours at 25° and finally at reflux for 4 hours. The resulting solution is washed with saturated aqueous NaCl solution and then saturated aqueous $Na_2CO_3$ solution and concentrated in vacuo to give crude 2-chloropyrazine-1,4-dioxide.

The crude 2-chloropyrazine-1,4-dioxide, 20 g., is stirred 4 hours with 50 ml. benzenesulfonyl chloride at 50° under $N_2$ and quenched on a mixture of ice, pyridine and saturated NaCl solution. The precipitated 2,6-dichloropyrazine-1-oxide is collected by filtration and converted to the title compound by reaction with piperazine as in Example 1.

EXAMPLE 3

6-Chloro-2-(1'-piperazinyl)-pyrazine-4-oxide

Similarly to Example 2, 2,6-dichloropyrazine is converted to the 4-oxide with 1.8 molar equivalents of trifluoroperacetic acid. The crude 2,6-dichloropyrazine-4-oxide is converted to the title compound by reaction with piperazine as in Example 1.

Example 4

Preparation of Capsule Formulation

| Ingredient | Milligrams per Tablet |
|---|---|
| 6-Chloro-2-(1'-piperazinyl)-pyrazine hydrochloride | 6 |
| Starch | 87 |
| Magnesium stearate | 7 |

The active ingredient, starch and magnesium stearate are blended together. The mixture is used to fill hard shell capsules of a suitable size at a fill weight of 100 milligrams per capsule.

Example 5

Preparation of Tablet Formulation

| Ingredient | Milligrams per Tablet |
|---|---|
| 6-Chloro-2-(1'-piperazinyl)-pyrazine hydrochloride | 12 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of active ingredient.

Example 6

Preparation of Oral Syrup Formulation

| Ingredient | Amount |
|---|---|
| 6-Chloro-2-(1'-piperazinyl)-pyrazine hydrochloride | 25 mg. |
| Sorbitol solution (70% N.F.) | 40 ml. |
| Sodium benzoate | 150 mg. |
| Sucaryl | 90 mg. |
| Saccharin | 10 mg. |
| Cherry Flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

EXAMPLE 7

On the day immediately preceding the test day (control day) the food consumption is measured for groups of from 7 to 10 rats allowed access to food for only 2 hours per day. On the next day (test day) the rats are injected i.p. with different dose levels of the test compound 3 minutes prior to commencement of the 2-hour feeding period. Food consumption on the test day is then measured and compared (paired t-test) with consumption on the control day. The results are set forth in the following table.

| Dose of 6-chloro-2-(1-piperazinyl)pyrazine hydrochloride mg./kg. i.p. | Grams Eaten on Control Day | Grams Eaten on Test Day |
| --- | --- | --- |
| 1.5 | $14.2 \pm 2.5^a$ | $7.5 \pm 2.0^a$ |

$^a$Standard Deviation.

What is claimed is:

1. 6-Chloro-2-(1'-piperazinyl)pyrazine, or N-oxide or a pharmaceutically acceptable salt thereof.
2. An anorexic pharmaceutical composition comprising a pharmaceutical carrier and an effective amount of 6-chloro-2-(1'-piperazinyl)pyrazine or N-oxide or a pharmaceutically acceptable salt thereof.
3. A method of producing an anorexic effect which comprises administering to a patient in need of such treatment an effective amount of 6-chloro-2-(1'-piperazinyl)pyrazine or N-oxide, or a pharmaceutically acceptable salt thereof.

* * * * *